United States Patent [19]

Miyake et al.

[11] 4,239,892

[45] Dec. 16, 1980

[54] PROCESS FOR PREPARING PYRIDINE BASES

[75] Inventors: Tetsuya Miyake, Tokyo; Kohji Noguchi; Kazuo Imamura, both of Yokohama, all of Japan

[73] Assignee: Asahi Kasei Kogyo Kabushiki Kaisha, Osaka, Japan

[21] Appl. No.: 61,335

[22] Filed: Jul. 27, 1979

Related U.S. Application Data

[62] Division of Ser. No. 841,083, Oct. 11, 1977, Pat. No. 4,179,576.

[30] Foreign Application Priority Data

Oct. 27, 1976 [JP] Japan .................. 51-128192
Oct. 27, 1976 [JP] Japan .................. 51-128194
Oct. 27, 1976 [JP] Japan .................. 51-128195

[51] Int. Cl.$^3$ ........................... C07D 213/10
[52] U.S. Cl. .......................... 546/251; 546/250
[58] Field of Search .................... 546/250, 251

[56] References Cited

U.S. PATENT DOCUMENTS

| | | | |
|---|---|---|---|
| 2,523,580 | 9/1950 | Mahan | 546/251 |
| 2,698,849 | 1/1955 | Aries | 546/251 |
| 3,829,428 | 8/1974 | Hargis | 546/251 |

FOREIGN PATENT DOCUMENTS

| | | | |
|---|---|---|---|
| 36-21536 | 11/1961 | Japan | 546/251 |
| 46-39873 | 11/1971 | Japan | 546/251 |
| 47-44745 | 11/1972 | Japan | 546/251 |
| 900799 | 7/1962 | United Kingdom | 546/251 |

*Primary Examiner*—Alan L. Rotman
*Attorney, Agent, or Firm*—Sprung, Felfe, Horn, Lynch & Kramer

[57] ABSTRACT

A process for preparing simultaneously pyridine bases including 2-methylpyridine and 4-methylpyridine, occasionally, together with pyridine from acetaldehyde and ammonia by gas phase catalytic reaction, characterized in that the gas phase catalytic reaction is conducted in the presence of a catalyst prepared by (A) incorporating at least one compound containing at least one metal selected from the group consisting of tungsten, manganese, nickel, iron, cobalt, molybdenum, uranium, lead, silver, copper and tin into silica-alumina simultaneously with preparation of the silica-alumina, or (B) subjecting silica-alumina to ion exchange with ions of at least one metal selected from the group consisting of manganese, nickel, iron, cobalt, uranium, lead, silver, copper and tin to adsorb the ions on said silica-alumina. According to the process of the present invention, there can be obtained the desired pyridine bases in high yield, whereas formation of by-products including high boiling point pyridine derivatives is remarkably suppressed. The catalyst employed in the present process has a high resistance to the reaction atmosphere.

12 Claims, No Drawings

PROCESS FOR PREPARING PYRIDINE BASES

This is a division of application Ser. No. 841,083, filed Oct. 11, 1977, now U.S. Pat. No. 4,179,576 issued Dec. 18, 1979.

The present invention relates to a process for preparing pyridine bases from acetaldehyde and ammonia by gas phase catalytic reaction. More particularly, the invention relates to a process for preparing simultaneously 2-methylpyridine and 4-methylpyridine, or simultaneously 2-methylpyridine, 4-methylpyridine and pyridine.

Pyridine bases are valuable intermediates for use in production of dyes, medicines, agricultural chemicals and the like, and they are important also as solvents. Moreover, corresponding vinyl monomers are prepared from 2- or 4-methylpyridines, and their application fields are now expanding because such vinyl monomers are suitable as comonomers for production of synthetic rubbers or synthetic fibers.

The process for preparing pyridine bases from acetaldehyde and ammonia by gas phase catalytic reaction is known as Chichibabin process, and its various improved processes have been proposed. In these known processes, however, the yields of pyridine bases, especially 2-methylpyridine, 4-methylpyridine and pyridine are relatively poor, and byproducts which render the purification step difficult, such as high boiling point pyridine bases, e.g., 2-methyl-5-ethylpyridine, 4-methyl-3-ethylpyridine, 4-propylpyridine and 2-propylpyridine, and other tar-like by-products are formed in large quantities. Moreover, catalysts used in these known processes have poor resistance to fouling.

It is therefore a primary object of the present invention to provide a process for preparing pyridine bases, especially 2-methylpyridine, 4-methylpyridine and pyridine, in high yields from acetaldehyde and ammonia by gas phase catalytic reaction using a durable catalyst to this reaction.

Another object of the present invention is to provide a process in which formation of high boiling point pyridine bases can be suppressed in the above gas phase catalytic reaction.

In general, the mechanism for formation of pyridine bases from acetaldehyde and ammonia is considered to include a complex combination of aldol condensation, Michael condensation and similar reactions. It is considered that when these condensation reactions are effected by the gas phase catalytic reaction, acid sites of the solid catalyst act as active points. Accordingly, the activity or performance of the catalyst used varies greatly depending on the number and intensity of acid sites of the solid catalyst.

The inventors of the present invention made investigations, using silica-alumina as the solid acid, on modification of this solid acid, especially on methods for modifying the solid acidity of silica-alumina. As a result, they found an optimum combination of a specific modifying metal with a specific modifying method, and succeeded in developing a process in which the yeilds of pyridine bases (exclusive of high boiling point pyridine bases) can be increased to those as high as 87%. Based on these findings, they have now completed the present invention.

More specifically, in accordance with the present invention, there is provided a process for preparing pyridine bases from acetaldehyde and ammonia by gas phase catalytic reaction, wherein the gas phase catalytic reaction is carried out at a temperature of 300° to 550° C. and at a space velocity of 200 to 10,000 hr$^{-1}$ in the presence of a catalyst prepared by (A) incorporating at least one compound containing at least one metal selected from the group consisting of tungsten, manganese, nickel, iron, cobalt, molybdenum, uranium, lead, silver, copper and tin into silica-alumina simultaneously with preparation of the silica-alumina, or (B) subjecting silica-alumina to ion exchange with ions of at least one metal selected from the group consisting of manganese, nickel, iron, cobalt, uranium, lead, silver, copper and tin to adsorb the ions on said silica-alumina.

As mentioned above, in the present invention there is employed a catalyst comprising silica-alumina and at least one modifying metal selected from the group consisting of W, Mn, Ni, Fe, Co, Mo, U, Pb, Ag, Cu and Sn in the form of a compound or ion.

In the catalyst of the present invention, it is preferred that the silica/alumina weight ratio is in the range of from 98/2 to 50/50, especially from 95/5 to 70/30.

When the modifying metal is incorporated in the form of a compound, it is advantageous that the metal compound should be incorporated in an amount of 1 to 70 parts by weight per 100 parts by weight of the sum of silica and alumina. When the modifying metal is selected from W, Mn, Co, Pb, U, Cu and Ag and it is incorporated in the form of a compound, it is preferred that the amount of the metal compound is 1 to 50 parts by weight per 100 parts by weight of the sum of silica and alumina. When a metal selected from the group consisting of Ni, Fe, Mo and Sn is used as the modifying metal and it is incorporated in the form of a compound, it is preferred that the compound is incorporated in an amount of 1 to 20 parts by weight per 100 parts by weight of the sum of silica and alumina. As the modifying metal to be incorporated in the form of a compound, there are advantageously employed W, Pb and Sn.

When the modifying metal is incorporated in the form of an ion by ion exchange adsorption, the adsorbed amount of the metal is generally 0.01 to 1.2 milliequivalents per gram of silica-alumina. When a metal selected from Pb, Mn, Co, U and Ag is used as the modifying metal, it is preferred that the absorbed amount of the metal is 0.1 to 1.2 milliequivalent per gram of silica-alumina, and when a metal selected from Ni, Fe and Sn is used as the modifying metal, it is preferred that the absorbed amount of the metal is 0.1 to 0.5 milliequivalent per gram of silica-alumina. As the modifying metal to be incorporated in the form of an ion, there are advantageously employed Pb and Sn.

As mentioned hereinbefore, the catalyst used in the present invention is prepared according to any of the following two methods:

(A) The modifying metal is incorporated in the form of a compound into silica-alumina simultaneously with preparation of the silica-alumina.

(B) The modifying metal is incorporated in the form of an ion in silica-alumina by ion exchange adsorption.

These two methods will now be described in detail.

Method (A)

A compound of a modifying metal present in a catalyst prepared according to the method (A) should be stable at the reaction temperature. Accordingly, oxides, sulfates, phosphates, halides and metal oxyacid salts of modifying metals are preferable. Some of such sulfates, phosphates, halides and metal oxyacid salts are water soluble, and some of them are relatively water-insoluble. Specifically stated, it is preferred that the modifying metals are present in the catalyst in the form of oxides such as $WO_3$, $MnO$, $NiO$, $Fe_2O_3$, $CoO$, $MoO_3$, $U_3O_8$, $PbO$, $Ag_2O$, $CuO$ and $SnO$, sulfates such as $MnSO_4$, $NiSO_4$, $Fe_2(SO_4)_3$, $CoSO_4$, $UO_2SO_4$, $PbSO_4$, $Ag_2SO_4$ and $CuSO_4$, phosphates such as $Mn_3(PO_4)_2$, $Ni_3(PO_4)_2$, $FePO_4$, $Co_3(PO_4)_2$, $Pb_3(PO_4)_2$ and $Ag_3PO_4$, halides such as $MnCl_2$, $MnF_2$, $NiCl_2$, $NiF_2$, $NiBr_2$, $FeF_3$, $CoCl_2$, $CoF_2$, $CoBr_2$, $UO_2Cl_2$, $PbCl_2$, $PbF_2$, $AgCl$, $AgF$, $AgBr$, $SnF_2$, $CuCl$, $CuF$ and $CuBr$, and metal oxyacid salts such as $Na_2WO_4$, $CaWO_4$, $FeWO_4$, $NiWO_4$, $PbWO_4$, $CoWO_4$, $Na_2MoO_4$, $PbMoO_4$, $NiMoO_4$ and $CaMoO_4$.

It is believed that in catalysts prepared according to the method (A), the modifying metals are present in the form of any of the foregoing compounds. It is also believed that more stable compounds may be formed by the reaction with silica, alumina, silicate ion, aluminum ion and the like, or by the change of the valency of the metal by calcination.

According to the method (A), as mentioned hereinbefore, it is essential that a compound of a modifying metal is incorporated into silica-alumina simultaneously with preparation of the silica-alumina. Stated illustratively, the three kinds of materials, namely silica source, alumina source and compound of modifying metal are put together and the compound of modifying metal is incorporated into the silica and the alumina. That is, simultaneously with the time when silica-alumina is prepared, for example, by a mixing method, a precipitation method, a cogelation method or the like, a compound of a modifying metal to be present in the resulting catalyst as it is or a precursor of said compound (a compound to be converted to the intended compound at the step of gel formation or calcination, for example, ammonium tungstate to be converted to the intended compound, tungsten oxide) is incorporated into silica and alumina and made copresent therewith. Differently stated, there are employed a method in which the compound of the modifying metal is incorporated, as it is, into the silica-alumina at the preparation of the latter to obtain a catalyst having the metal compound in the form of a water-soluble or relatively water-insoluble compound; and a method in which the precursor of the intended compound containing the modifying metal is incorporated in the silica-alumina at the preparation of the latter to obtain a catalyst having the metal compound in the form of an oxide. In this case, the precursor is converted to said intended compound, for example the oxide at the stage of calcination.

As the silica source, there may be used silica hydrogel, silica sol, sodium silicate, alkylsiloxanes, silicon tetrachloride, etc., and as the alumina source, there may be used alumina hydrogel, alumina sol, aluminum salts such as aluminum sulfate, aluminum chloride and aluminum nitrate, sodium aluminate, aluminum isopropoxide, etc.

In preparing the catalyst according to the method (A), the modifying metal may be used in the form of a water-soluble compound and added to a reaction mixture for forming silica-alumina. Organic and inorganic salts may be used as the water-soluble compound. As the organic salt, water-soluble formic acid salts, acetic acid salts, propionic acid salts, lactic acid salts, oxalic acid salts and citric acid salts are preferably used. As the inorganic salt, water-soluble nitrates, sulfates, halides and metal oxyacid salts are preferably used. More specifically, there are preferably employed manganese formate, nickel formate, ferric formate, cobalt formate, uranyl formate, cupric formate, manganese acetate, nickel acetate, ferric acetate, cobalt acetate, uranyl acetate, cupric acetate, lead acetate, stannous acetate, silver acetate, manganese propionate, cobalt propionate, manganese lactate, ferric lactate, silver lactate, ferric oxalate, ferric citrate, cobalt citrate, $Mn(NO_3)_2$, $Ni(NO_3)_2$, $Fe(NO_3)_3$, $Co(NO_3)_2$, $Cu(NO_3)_2$, $Pb(NO_3)_2$, $UO_2(NO_3)_2$, $AgNO_3$, $MnSO_4$, $NiSO_4$, $Fe_2(SO_4)_3$, $CoSO_4$, $UO_2SO_4$, $CuSO_4$, $MnCl_2$, $NiCl_2$, $FeCl_3$, $CoCl_2$, $UO_2Cl_2$, $CuCl_2$, ammonium paratungstate, ammonium paramolybdate, sodium tungstate, potassium tungstate, sodium molybdate and potassium molybdate, alone or in mixture.

When the modifying metal is to be in the form of an oxide in the resulting catalyst, the metal compound may be once converted to a hydroxide by neutralization or the like, unless it provides an oxide by calcination in the air. In general, the starting metal compounds are preferably to be converted to a hydroxide by neutralization or the like. The conversion to hydroxide may be effected by adjusting the pH of aqueous solution of the metal compounds more than 6, or more preferably to 6 to 8. Moreover, the water-soluble compounds as given above may be employed in the form of a hydroxide slurry formed by hydrolysis of the compounds.

When a water-soluble compound of the modifying metal, other than an oxide, namely, a sulfate, phosphate, halide and metal oxyacid salt, is present in the resulting catalyst, a compound stable at the reaction temperature is chosen from the water-soluble compounds as given above, and silica-alumina is prepared in the presence of this compound. As the specific example of the compound stable at the reaction temperature, $MnSO_4$, $NiSO_4$, $Fe_2(SO_4)_3$, $CoSO_4$, $UO_2SO_4$, $CuSO_4$, $MnCl_2$, $NiCl_2$, $CoCl_2$, $CoBr_2$, $UO_2Cl_2$, $NaWO_4$ and the like, are preferred. They may be employed alone or in mixture.

When a relatively water-insoluble compound of the modifying metal, other than an oxide, namely, a sulfate, phosphate, halide and metal oxyacid salt, is included in the resulting catalyst, silica-alumina is prepared in the presence of a water-soluble compound as given above while adding a precipitating agent to convert the water-soluble compound to the intended relatively water-insoluble compound. When a chloride precipitate such as $PbCl_2$ or $AgCl$, for example, is to be included in the catalyst, $HCl$, $NaCl$, $KCl$ and the like are used as the precipitating agents; when a fluoride precipitate such as $MnF_2$, $NiF_2$, $FeF_3$, $CoF_2$, $PbF_2$, $AgF$ or $SnF_2$ is incorporated in the resulting catalyst, $NaF$, $NH_4F$, $KF$ and the like are used as the precipitating agents. When a sulfate precipitate such as $PbSO_4$ or $Ag_2SO_4$ is incorporated in the resulting catalyst, $H_2SO_4$, $Na_2SO_4$ and the like are used as the precipitating agents; when a phosphate precipitate such as $Mn_3(PO_4)_2$, $Ni_3(PO_4)_2$, $FePO_4$, $Co_3(PO_4)_2$ or $Pb_3(PO_4)_2$ is included in the resulting catalyst, $H_3PO_4$, $Na_3PO_4$, $K_3PO_4$, $(NH_4)_3PO_4$, $Na_2HPO_4$, $K_2HPO_4$, $(NH_4)_2PO_4$ and the like are used as the precipitating agents.

Methods similar to the mixing, precipitation and cogelation methods adopted for preparation of silica-alumina are used for the production of the catalyst of the present invention. The following methods are the examples to be employed to prepare a catalyst in this invention.

(1) When the modifying metal is present in the form of an oxide in the final catalyst:

(a) An aqueous solution of a compound of the modifying metal is added to a mixture of silica in the form of silica hydrogel and/or silica sol and alumina in the form of alumina hydrogel and/or alumina sol. The resulting mixture is sufficiently stirred by means of a stirrer, kneader or the like, and the pH is adjusted to at least 6, preferably 6 to 8. The stirring is further conducted; the resulting gelatinous slurry is filtered; the recovered solid is sufficiently washed with water and dried at 80° to 130° C. for 4 to 10 hours. Then, the particle size is adjusted by pulverization or the dried solid is shaped according to a customary method. Finally, the pulverized or shaped solid is calcined at 350° to 550° C. for 4 to 8 hours.

(b) An aqueous solution of an aluminum salt and an aqueous solution of a compound of the modifying metal are simultaneously added to silica hydrogel and/or silica sol, and the resulting liquid is sufficiently mixed. Then, the pH is adjusted to at least 6, preferably 6 to 8, and the mixing is further conducted sufficiently. The resulting gelatinous slurry is then treated in substantially the same manner as described in (a) above.

(c) An aqueous solution of sodium silicate, an aqueous solution of an aluminum salt and an aqueous solution of a compound of the modifying metal are mixed together in a container in which mixing is done in a short time, for example, with a mixer, and the pH is adjusted to at least 6, preferably 6 to 8. Then, the mixing is further conducted sufficiently. The resulting gelatinous slurry is then treated in substantially the same manner as described in (a) above.

(d) In any of the foregoing methods (a) to (c), a slurry of a hydroxide of the modifying metal, which has been prepared by hydrolysis in advance, is used in place of the aqueous solution of the modifying metal compound. The slurry is then treated in substantially the same manner as described in any of (a) to (c) above.

In each of the foregoing methods, the pH adjustment is accomplished by using an acid or alkali. As the acid, an aqueous solution of hydrochloric acid, sulfuric acid, nitric acid, acetic acid or the like is preferably used. As the alkali, an aqueous solution of sodium hydroxide, potassium hydroxide, ammonia or the like is preferably used. Some modifying metals form relatively insoluble salts or soluble complex salts with a certain acid or alkali. Therefore, a suitable acid or salt should be used to prevent formation of such metal compounds other than metal hydroxy precipitates.

(2) When the modifying metal is present in the form of a water-soluble compound other than an oxide in the final catalyst:

An aqueous solution of a compound of the modifying metal is added to a mixture of silica in the form of silica hydrogel and/or silica sol and alumina in the form of alumina hydrogel and/or alumina sol, and the mixture is sufficiently stirred by means of a stirrer, kneader or the like. Even if silica sol or alumina sol is used as the silica or alumina source, the metal compound to be added simultaneously acts as an electrolyte and breaks down the ionic balance which has stabilized colloidal particles. Thus, gelation of silica and alumina sols may sufficiently advances. Even if gelation does not take place, it is advantageous to cause gelation by heating under such conditions as will not modify the metal compound by hydrolysis or double decomposition, or to cause gelation by adding a metal-free coagulant. The resulting gelatinous slurry is subjected to filtration and the recovered solid is appropriately washed with water under such conditions as will not cause complete dissolution of the metal compound contained therein. The washed solid is then treated in substantially the same manner as described in (1)-(a) above.

Metal compounds such as $MnSO_4$, $NiSO_4$, $Fe_2(SO_4)_3$, $CoSO_4$, $UO_2SO_4$, $CuSO_4$, $MnCl_2$, $NiCl_2$, $CoCl_2$, $NiBr_2$, $CoBr_2$, $UO_2Cl_2$, $Na_2WO_4$, and $Na_2MoO_4$, for example, are suitable to be incorporated in the resulting catalyst according to the method (2).

(3) When the modifying metal is present in the form of a relatively water-insoluble compound in the final catalyst:

An aqueous solution of a precursor of the intended compound of the modifying metal compound is added to a mixture of silica in the form of silica hydrogel and/or silica sol and alumina in the form of alumina hydrogel and/or alumina sol, and the mixture is sufficiently stirred by a stirrer, kneader or the like. Then a precipitating agent capable of double-decomposing with the precursor of the intended compound of the modifying metal and precipitating the modifying metal in the form of a relatively water-insoluble salt is added to the mixture. The resulting gelatinous slurry is sufficiently stirred and filtered, and the recovered solid is sufficiently washed with water and then treated in substantially the same manner as described in (1)-(a) above.

As the compound of the modifying metal that is included in the resulting catalyst according to this method, there can be mentioned, for example, $PbSO_4$, $Ag_2SO_4$, $MnF_2$, $NiF_2$, $FeF_3$, $CoF_2$, $PbF_2$, $AgF$, $CuF$, $SnF_2$, $PbCl_2$, $AgCl$, $CuCl$, $AgBr$, $CuBr$, $Mn_3(PO_4)_2$, $Ni_3(PO_4)_2$, $FePO_4$, $Co_3(PO_4)_2$, $Pb_3(PO_4)_2$, $Ag_3PO_4$, $CaWO_4$, $PbWO_4$, $FeWO_4$, $MnWO_4$, $CoWO_4$, $PbMoO_4$, $NiMoO_4$ and $CaMoO_4$.

As will be apparent from the foregoing illustration, according to the method (A), the modifying metal is incorporated in the form of a compound in the catalyst simultaneously with preparation of silica-alumina.

Method (B)

According to the method (B), the modifying metal is incorporated in the form of an ion in the catalyst of the present invention by ion exchange adsorption. By the term "ion exchange adsorption" is meant the operation or reaction for making ions of the modifying metal adsorbed tightly on silica-alumina at its acid sites while forming a metal salt of silica-alumina according to ion exchange, and by the term "ion exchange-adsorbed state" is meant the state where ions of the modifying metal are strongly adsorbed on silica-alumina at its acid sites in the form of a metal salt of silica-alumina. In the catalyst prepared by the method (B), it is exactly unknown but believed that the modifying metal is ion exchange-adsorbed on silica-alumina substantially in the form of an ion, but a part of the modifying metal may be contained in the metallic state or in the form of a compound.

In the catalyst prepared according to the method (B), the modifying metal is ion exchange-adsorbed on silica-alumina in the form of an ion. However, if a solution containing the modifying metal ion that is to be incorporated in a silica-alumina catalyst according to the present invention is directly treated with silica-alumina, the modifying metal ion is hardly ion exchange-adsorbed on the silica-alumina. Accordingly, there is adopted a method in which a solution containing an ion capable of being directly ion exchange-adsorbed on silica-alumina is first treated with silica-alumina to convert the ion to a salt of silica-alumina and then a solution containing the modifying metal ion is treated with silica-alumina and adsorbed thereon by ion exchange adsorption. As the ion capable of being directly ion exchange-adsorbed on silica-alumina (hereinafter referred to as "medium ion"), there can be mentioned, for example, $Li^+$, $Na^+$, $K^+$, $Ca^{++}$, $Mg^{++}$ and $NH_4^+$. Among these medium ions, an ammonium ion is most preferred.

According to the method (B), by dipping silica-alumina in an aqueous solution containing 0.1 to 2.0 moles/liter of a medium ion or passing this aqueous solution through a column packed with silica-alumina, silica-alumina is converted to a silica-alumina salt of the medium ion. In this case, it is preferred that calcined silica-alumina is used as the silica-alumina. When the so formed silica-alumina salt of the medium ion (medium ion type silica-alumina) is contacted with an aqueous solution containing a modifying metal ion, cation exchange reaction is caused between the medium ion and the modifying metal ion to provide silica-alumina having the modifying metal ion exchange-adsorbed thereon.

Cation exchange can be performed by a customary batch method or a column method. According to the batch method, medium ion type silica-alumina is dipped in an aqueous solution containing modifying metal ions. According to the column method, medium ion type silica-alumina is packed in a column and development is carried out with an aqueous solution containing modifying metal ions.

As the aqueous solution containing modifying metal ions, there can be used aqueous solutions of organic and inorganic salts of the modifying metal. As the organic salt, there are preferably employed a formic acid salt, an acetic acid salt, a propionic acid salt, a lactic acid salt, an oxalic acid salt and a citric acid salt. As the inorganic salt, there are preferably employed a nitric acid salt, a sulfuric acid salt, a halide and an ammonium complex salt. More specifically, aqueous solutions of manganese formate, nickel formate, ferric formate, cobalt formate, uranyl formate, cupric formate, manganese acetate, nickel acetate, iron acetate, cobalt acetate, copper acetate, lead acetate, manganese propionate, manganese lactate, iron lactate, iron oxalate, iron citrate, $Mn(NO_3)_2$, $Ni(NO_3)_2$, $Fe(NO_3)_3$, $Co(NO_3)_2$, $Cu(NO_3)_2$, $Pb(NO_3)_2$, $UO_2(NO_3)_2$, $AgNO_3$, $MnSO_4$, $NiSo_4$, $Fe_2(SO_4)_3$, $CoSO_4$, $UO_2SO_4$, $CuSO_4$, $MnCl_2$, $NiCl_2$, $FeCl_3$, $CoCl_2$, $UO_2Cl_2$, $CuCl_2$, $CuCl$, $SnCl_2$, $[Co(NH_3)_6]Cl_2$, $[Ni(NH_3)_6]Cl_2$, $[Ag(NH_3)_2]Cl$ and $[Cu(NH_3)_2]Cl$ are preferably employed.

In general, the concentration of the aqueous solution is adjusted to 0.01 to 2.0 moles/liter as the salt, and it is preferred that the concentration of the aqueous solution is in the range of from 0.05 to 0.5 mole/liter. It also is preferred that the amount of the modifying metal ions in the aqueous solution is in the range of from 1 to 50 millimoles per gram of silica-alumina. The pH of the modifying metal ion-containing aqueous solution is adjusted to a range in which hydrolysis of the metal ions is not caused. The pH adjustment is accomplished by an acid or alkali. As the acid, there are employed aqueous solutions of hydrochloric acid, sulfuric acid, nitric acid, acetic acid and the like, and as the alkali, there are used aqueous solutions of ammonia, sodium hydroxide, potassium hydroxide and the like. However, use of a combination of a modifying metal and an acid or alkali, which will result in formation of a relatively water-insoluble salt, should be avoided.

When two or more modifying metal ions are ion exchange-adsorbed in silica-alumina, the foregoing procedures are conducted by using an aqueous solution of mixed salts. However, in the case where a relatively water-insoluble salt is formed or unavoidable hydrolysis takes place, there may be adopted a staged method in which one modifying metal ion is adsorbed by ion exchange and after sufficient water-washing, the other modifying metal ion is adsorbed by ion exchange.

It is preferred that the so formed modifying metal ion type silica-alumina is sufficiently washed with deionized water until a metal ion is not detected in the washing water. The so formed modified silica-alumina is then dried at 80° to 130° C. for 2 to 10 hours, and after it has been molded into tablets according to need, it is calcined at 300° to 550° C. for 4 to 8 hours.

The catalyst according to the above-mentioned method (B) is distinguishable over a catalyst prepared according to a customary impregnation method. More specifically, even if silica-alumina is dipped in an aqueous solution of the above-mentioned metal salt that is used in the present invention according to the customary impregnation technique, the above-mentioned ion exchange adsorption is not caused but the metal salt is merely deposited on the surface of silica-alumina. Accordingly, in this state, bonding between the modifying metal and silica-alumina is very weak and the modifying metal is readily dissolved out by water washing. In contrast, in the present invention, since silica-alumina is first converted to a medium ion type silica-alumina by treating silica-alumina with an aqueous solution containing medium ions and this medium ion type silica-alumina is reacted with an aqueous solution containing modifying metal ions to form silica-alumina having the modifying metal ions adsorbed thereon by ion exchange, bonding between the modifying metal ions and silica-alumina is very strong and the modifying metal ions are not dissolved out by water-washing.

In the instant specification, the so prepared catalyst is expressed as SA-$\overline{M(n)}$ in which M represents a modifying metal ion and n indicates the valency of the modifying metal ion, and the catalyst prepared by impregnation is expressed as SA-MX in which MX represents a metal compound.

In practising the process of the present invention, the catalyst prepared according to the method (A) or (B) is packed in a reaction tube and the starting material vapor is fed to the reaction tube while maintaining the catalyst layer at 300° to 550° C. It is preferred that the starting material vapor is preheated to 300° to 550° C. prior to introduction to or contact with the catalyst layer. Deposition of a crystal of acetaldehyde ammonium which may cause clogging in pipes can be avoided by preheating acetaldehyde and ammonia independently to a temperature of at least 200° C. and then mixing them. A high temperature vapor coming from the reaction tube is condensed by a cooler. Results of the reaction can be grasped by gas chromatograph analysis of the product.

As the starting material, there may be used acetaldehyde per se or a compound capable of being decomposed at the reaction temperature to provide acetaldehyde. Namely, paraaldehyde or metaaldehyde may be used.

The molar ratio of ammonia to acetaldehyde is generally at least 0.3, preferably in the range of 0.5 to 3.0.

The reaction may be carried out in the presence or absence of an inert substance which is gaseous at the reaction temperature and does not participate directly in the reaction. Since the present reaction is highly exothermic, it is preferred to remove the heat generated by the reaction. Therefore, the reaction is preferably carried out in the presence of an inert gas such as steam, nitrogen, argon or helium as a diluent. In general, the inert gas is present in an amount of 0 to 90% by volume based on the starting material vapor. It is preferred that the amount of the inert gas is 25 to 85% by volume based on the starting material vapor.

The reaction may be carried out under reduced or elevated pressure, namely under a pressure of 0.1 to 10 atmospheres, but in general, the reaction is conducted under atmospheric pressure.

As mentioned hereinbefore, the reaction temperature at which the process of the present invention is worked is in the range of 300° to 550° C., and it is preferred that the reaction is carried out at 350° to 550° C. When the reaction temperature is too low, the conversion is low and acetaldehyde is mainly recovered in the form of acetaldehyde ammonium, and when the reaction temperature is too high, decomposition or carbonization of the product is remarkably increased and the yield of the intended product is lowered.

It is important that the process of the present invention is conducted at a space velocity of 200 to 10,000 hr$^{-1}$, preferably 400 to 2,000 hr$^{-1}$. An optimum space velocity is varied depending on the reaction temperature, the kind and particle size of the catalyst used, the gas composition and other factors but the optimum velocity can readily be determined by conducting simple experiments while fixing the foregoing conditions. In general, if the space velocity is lower than 200 hr$^{-1}$, even after complete conversion the product gas is kept in contact with the catalyst, resulting in advance of decomposition and carbonization of the resulting pyri- TABLE 1-continued

| Catalyst | Preparation Method | Yields(%) of Products | | |
|---|---|---|---|---|
| | | 2-methyl-pyridine | 4-methyl-pyridine | total |
| SA—WO$_3$ | impregnation method | 20.5 | 20.7 | 41.2 |
| SA—Pb(II) | method(B) of present invention | 43.1 | 39.5 | 82.6 |
| SA—PbO | impregnation method | 29.4 | 25.4 | 54.8 |
| | Reaction temperature: | 440° C. | | |
| | Space velocity: | 800 hr$^{-1}$ | | |

(Data shown in Table 1 are maximum yields obtained in experiments conducted by the inventors of the present invention.)

In the catalyst prepared according to the impregnation method, the modifying metal compound only adheres to silica-alumina, and it is not distributed uniformly but unevenly in an islands-in-sea manner. Therefore, the effect of the modifying metal compound cannot be manifested sufficiently.

On the other hand, in the catalyst prepared according to the method (A) of the present invention, silica, alumina and the modifying metal compound are mixed together highly homogeneously. Also in such catalyst, it is construed that active sites are acid sites generated by bonding of silica and alumina. However, when bonding of silica and alumina is formed, since the modifying metal is included in the skeleton structure of silica-alumina, acid sites generated by bonding of silica and alumina are influenced in a complicated manner by the included modifying metal compound and the resulting catalyst shows a solid acidity different from that of the conventional silica-alumina catalyst.

metal, if the content of the modifying metal is too high, acetonitrile is readily formed as a by-product and the yield of the intended pyridine bases is lowered. Accordingly, when a modifying metal as mentioned above is employed, an optimum content of the modifying metal is relatively low.

Among catalysts that are used in the process of the present invention, those containing at least one modifying metal selected from Ag and Cu can enhance the yield of pyridine among the yields of the intended pyridine bases. In this case, it is preferred to adopt the method (B) for the preparation of the catalyst, and it also is preferred that the valency of Ag and Cu is 1. Moreover, when Ag or Cu is used as the first metal, it is preferred that at least one second metal selected from the group consisting of Sn, Pb, Mn, Cd, Zn, Co, Ni, Fe, alkali metals such as Na and K and alkaline earth metals such as Ca and Mg is used in combination with the first metal. In this case, the total yield of pyridine, 2-methylpyridine and 4-methylpyridine can be further improved. In catalysts of this type, it is preferred that the content of the first metal is 0.1 to 1.0 milliequivalent per gram of silica-alumina, the content of the second metal is 0.01 to 1.0 milliequivalent per gram of silica-alumina and the total content of the first and second metals is up to 1.2 milliequivalent per gram of silica-alumina. Among the second metals as given above, Pb, Sn, Ca and Cd may be most advantageously employed.

In the process of the present invention, the yield of the intended pyridine bases can be remarkably improved as mentioned hereinbefore, and in addition, the resistance of the catalyst can also be improved remarkably. More specifically, when the reaction is conducted for 10 hours by using a customary silica-alumina catalyst, the total yield of 2-methylpyridine and 4-methylpyridine is reduced to 30.1% from the initial value of 43.9%; namely, the yield is reduced by 31% based on the initial value. In contrast, in a $SiO_2-Al_2O_3-WO_3$ catalyst prepared according to the method (A) of the present invention, the yield is reduced only to 73.6% from the initial value of 79.1%, and reduction of the yield is only 7% based on the initial value. Further, in a SAP5 (II) catalyst prepared according to the method (B), the yield is reduced to 79.6% from the initial value of 83.0% and reduction of the yield is only 4% based on the initial value. This prominent improvement of the yield is deemed to be due to the fact that the selectivity to the intended reaction is enhanced to reduce formation of high boiling point pyridine bases and carbonization is hardly caused on the surface of the catalyst. In the present invention, the degraded catalyst can easily be regenerated by passing streams of an oxygen-containing gas through the degraded catalyst.

The present invention will now be described in detail by reference to the following Examples that by no means limit the scope of the invention.

Unless otherwise specified, the percentage, part, ratio etc. appearing in the Examples are given by weight.

EXAMPLE 1

A solution of 97.9 parts of aluminum sulfate [$Al_2(SO_4)_3 \cdot 16-18H_2O$] in 500 ml of water and a solution of 30 parts of ammonium paratungstate in 2,000 ml of warm water were added to 283 parts of silica sol having a silica content of 30%, and the resulting mixture was agitated for 2 hours. Then, the pH of the mixture was adjusted to 8 by addition of aqueous ammonia, whereby the liquid mixture was gelled. The gelled slurry was agitated for 4 hours and allowed to stand still at room temperature for two days and two nights.

The resulting gel was subjected to filtration, and the recovered solid was sufficiently washed, dried at 100° C. for 4 hours, pulverized and calcined for 4 to 8 hours in an air current. The so obtained catalyst had a silica/alumina/tungsten oxide ratio of 85/15/25.

A reaction tube was packed with 100 ml of the so prepared catalyst, and a gas phase catalytic reaction was carried out while introducing a gas mixture of acetaldehyde and ammonia (1:1.5) at a reaction temperature of 430° C. and a space velocity of 1,000 $hr^{-1}$. As a result, 2-methylpyridine and 4-methylpyridine were obtained in yields of 33.2% and 35.8%, respectively, and the total yield of the two pyridine bases was 69.0%

EXAMPLE 2

By using the same catalyst as used in Example 1, a gas phase catalytic reaction was carried out while introducing a gas mixture of acetaldehyde, ammonia, steam and nitrogen (1:1:4:2 by volume) at a reaction temperature of 440° C. and a space velocity of 800 $hr^{-1}$. The yields of 2-methylpyridine and 4-methylpyridine were 33.7% and 46.1%, respectively, and the total yield of the two pyridine bases was 79.8%.

EXAMPLE 3

By using a catalyst prepared substantially the same method as described in Example 1, which had a silica/alumina/tungsten oxide ratio of 85/15/4, a gas phase catalytic reaction was carried out under the same reaction conditions as described in Example 2. As a result, 2-methylpyridine and 4-methylpyridine were obtained in yields of 24.3% and 32.5%, respectively, and the total yield of the two pyridine bases was 56.8%.

COMPARATIVE EXAMPLE 1

A gas phase catalytic reaction was carried out under the same conditions as described in Example 2 by using silica-alumina and silica-alumina-tungsten oxide catalysts prepared according to the impregnation method. Obtained results are shown in Table 2.

TABLE 2

| | | Yields (%) of Products | | |
|---|---|---|---|---|
| Run No. | Composition of Catalyst | 2-methyl-pyridine | 4-methyl-pyridine | total |
| 1 | SA—WO$_3$ (100:4) | 20.5 | 20.7 | 41.2 |
| 2 | SA—WO$_3$ (100:10) | 16.4 | 16.4 | 32.8 |
| 3 | SA (85:15) | 16.2 | 24.7 | 40.9 |

SA has a silica/alumina ratio of 85/15

EXAMPLE 4

By using a catalyst having a silica/alumina/tungsten oxide ratio of 75/25/25, which was prepared in substantially the same manner as described in Example 1, a gas phase catalytic reaction was carried out under the same conditions as described in Example 2. As a result, 2-methylpyridine and 4-methylpyridine were obtained in yields of 30.4%, respectively, and the total yield of the two pyridine bases was 61.9%.

EXAMPLE 5

By using catalysts containing a metal oxide indicated in Table 3, which were prepared in substantially the same manner as described in Example 1, gas phase catalytic reactions were carried out under the same conditions as described in Example 2 to obtain results shown in Table 3. The precursors of the metal oxides and their amounts added are as follows:

Run No. 1: 40 parts of manganese nitrate
Run No. 2: 20 parts of nickel nitrate
Run No. 3: 25 parts of ferric nitrate
Run No. 4: 35 parts of uranyl nitrate
Run No. 5: 20 parts of stannous chloride
Run No. 6: 40 parts of lead nitrate

TABLE 3

| Run No. | Composition of Catalyst | Yields (%) of Products | | |
|---|---|---|---|---|
| | | 2-methyl-pyridine | 4-methyl-pyridine | total |
| 1 | $SiO_2$—$Al_2O_3$—MnO | 27.6 | 35.9 | 63.5 |
| 2 | $SiO_2$—$Al_2O_3$—NiO | 28.1 | 34.5 | 62.6 |
| 3 | $SiO_2$—$Al_2O_3$—$Fe_2O_3$ | 27.0 | 32.9 | 59.9 |
| 4 | $SiO_2$—$Al_2O_3$—$U_3O_8$ | 26.0 | 34.8 | 60.8 |
| 5 | $SiO_2$—$Al_2O_3$—SnO | 30.0 | 35.4 | 65.4 |
| 6 | $SiO_2$—$Al_2O_3$—PbO | 33.1 | 35.2 | 68.3 |

EXAMPLE 6

Catalysts containing molybdenum oxide in an amount of 5, 10, 20 40 parts per 100 parts of the sum of silica and alumina were prepared in substantially the same manner as described in Example 1 by using ammonium paramolybdate as the precursor of molybdenum oxide. By using these catalysts, gas phase catalytic reactions were carried out under the same conditions as described in Example 2 to obtain results shown in Table 4.

TABLE 4

| Run No. | Composition of Catalyst | | | Yields (%) of Products | | | |
|---|---|---|---|---|---|---|---|
| | $SiO_2$ | $Al_2O_3$ | $MoO_3$ | 2-methyl-pyridine | 4-methyl-pyridine | total | aceto-nitrile |
| 1 | 85 | 15 | 5 | 28.2 | 32.0 | 60.2 | 3.8 |
| 2 | 85 | 15 | 10 | 30.3 | 33.2 | 63.5 | 6.2 |
| 3 | 85 | 15 | 20 | 28.0 | 27.6 | 55.6 | 15.4 |
| 4 | 85 | 15 | 40 | 20.4 | 19.8 | 40.2 | 27.2 |

EXAMPLE 7

A slurry was prepared by mixing 283 parts of silica sol having a silica content of 30% with 150 parts of alumina sol having an alumina content of 10% sufficiently, and an aqueous solution of 30 parts of manganese chloride in 500 ml of water was promptly added to the slurry. Gelation took place, but the gelled slurry was agitated sufficiently to obtain a homogeneous gelatinous slurry. The slurry was allowed to stand still for 2 days and nights, and the gel was recovered by filtration, washed with 1,000 ml of deionized water three times, dried at 100° C. for 4 hours, pulverized and calcined at 500° C. for 4 hours. In the resulting catalyst, the silica/alumina/manganese chloride ratio was 85/15/23.

By using the so obtained catalyst, a gas phase catalytic reaction was carried out under the same conditions as described in Example 2. As a result, 2-methylpyridine and 4-methylpyridine were obtained in yields of 26.0% and 39.3%, respectively, and the total yield of the two pyridine bases was 65.3%.

EXAMPLE 8

A catalyst was prepared in substantially the same manner as described in Example 7 except that 30 parts of manganese sulfate was used instead of the manganese chloride used in Example 7, and by using the so prepared catalyst, a gas phase catalytic reaction was carried out under the same conditions as described in Example 2. As a result, 2-methylpyridine and 4-methylpyridine were obtained in yields of 24.6% and 32.0%, respectively, and the total yield of the two pyridine bases was 56.6%.

EXAMPLE 9

A slurry was prepared by mixing 283 parts of silica sol having a silica content of 30% sufficiently with 150 parts of alumina sol having an alumina content of 10%, and an aqueous solution of 30 parts of manganese sulfate in 500 ml of water was promptly added to the slurry to obtain a gelatinous slurry, and while the resulting slurry was sufficiently agitated, an aqueous solution of 10 parts of ammonium fluoride in 100 ml of water was added thereto. The agitation was further conducted for 4 hours and the mixture was allowed to stand still for two days and two nights. The gel was recovered by filtration, washed sufficiently with deionized water, dried at 100° C. for 4 hours, pulverized and calcined at 500° C. for 4 hours to obtain a catalyst having a silica/alumina/manganese fluoride ratio of 85/15/10.

By using the so prepared catalyst, a gas phase catalytic reaction was carried out under the same conditions as described in Example 2 to obtain 2-methylpyridine and 4-methylpyridine in yields of 36.2% and 34.0%, respectively. The total yield of the two pyridine bases was 70.2%.

EXAMPLE 10

A catalyst having a silica/alumina/lead fluoride ratio of 85/15/18 was prepared in substantially the same manner as described in Example 9 except that 30 parts of lead nitrate was used instead of the manganese sulfate. By using the so prepared catalyst, a gas phase catalytic reaction was carried out under the same conditions as described in Example 2 to obtain 2-methylpyridine and 4-methylpyridine in yields of 37.0% and 34.3%, respectively. The total yield of the two pyridine bases was 71.3%.

EXAMPLE 11

A catalyst having a silica/alumina/lead phosphate ratio of 85/15/20 was prepared in substantially the same manner as described in Example 9 except that 30 parts of lead nitrate was used instead of the manganese sulfate and 40 parts of 30% phosphoric acid was used instead of the ammonium fluoride. By using the so prepared catalyst, a gas phase catalytic reaction was carried out under the same conditions as described in Example 2 to obtain 2-methylpyridine and 4-methylpyridine in yields of 35.4% and 32.8%, respectively. The total yield of the two pyridine bases was 68.2%.

EXAMPLE 12

Pelletized silica-alumina (having an alumina content of 13%) having a size of 1 mm, which had been calcined at 500° C. for 4 hours in an electric furnace, was dipped in 1 N aqueous ammonia for 7 days and then air-dried to obtain ammonium type silica-alumina.

A glass column having an inner diameter of 30 mm was packed with 100 ml of the so prepared ammonium type silica-alumina and 2,000 ml of an aqueous solution containing 0.4 mole of lead nitrate was developed over a period of 7 days. The so treated silica-alumina was washed sufficiently with deionized water until the lead ion was not detected in the washing liquid. Then, the treated silica-alumina was dried at 90° to 100° C. for 4 hours and calcined at 500° C. for 4 hours to obtain a catalyst containing 1.0 milliequivalent of lead per gram of silica-alumina.

A gas phase catalytic reaction was carried out under the same conditions as described in Example 2 by using the so prepared catalyst to obtain 2-methylpyridine and 4-methylpyridine in yields of 43.1% and 39.5%, respectively. The total yield of the two pyridine bases was 82.6%. The yields of pyridine and high boiling point pyridine bases were 0.8% and 1.2%, respectively.

EXAMPLE 13

Catalysts containing 0.4 milliequivalent and 0.2 milliequivalent of lead per gram of silica-alumina, respectively, were prepared in substantially the same manner as described in Example 12, and by using the so prepared catalysts, gas phase catalytic reactions were carried out under the same conditions as described in Example 2 to obtain results shown in Table 5.

COMPARATIVE EXAMPLE 2

By using catalysts containing 0.2 and 0.4 millimole of lead oxide per gram of silica-alumina, which were prepared according to the impregnation method and the silica-alumina, respectively, gas phase catalytic reactions were carried out under the same conditions as described in Example 2 to obtain results shown in Table 5.

ing 0.3 mole of manganese nitrate was used instead of the aqueous solution of lead nitrate.

Run No. 2:

A catalyst having a cobalt content of 0.6 milliequivalent per gram of silica-alumina was prepared in substantially the same manner as described in Example 12 except that 2,000 ml of an aqueous solution containing 0.3 mole of cobalt nitrate was used instead of the aqueous solution of lead nitrate.

Run No. 3:

A catalyst having a nickel content of 0.25 milliequivalent per gram of silica-alumina was prepared in substantially the same manner as described in Example 12 except that 2,000 ml of an aqueous solution containing 0.1 mole of nickel nitrate was used instead of the aqueous solution of lead nitrate.

Run No. 4:

A catalyst having an iron content of 0.28 milliequivalent per gram of silica-alumina was prepared in substantially the same manner as described in Example 12 except that 2,000 ml of an aqueous solution containing 0.1 mole of iron nitrate was used instead of the aqueous solution of lead nitrate.

Run No. 5:

A catalyst having a lead content of 0.5 milliequivalent per gram of silica-alumina and a nickel content of 0.2 milliequivalent per gram of silica-alumina was prepared in substantially the same manner as described in Exam-

TABLE 5

| | Catalyst | Yields (%) of Products | | | |
|---|---|---|---|---|---|
| | | 2-methl-pyridine | 4-methyl-pyridine | high boiling point pyridine | 2-methylpyridine plus 4-methyl-pyridine |
| Run No. 1 of Example 13 | SA—$\overline{Pb}$(II) (Pb content of 0.4 meq/g of SA) | 39.2 | 37.1 | 1.8 | 76.3 |
| Run No. 2 of Example 13 | SA—$\overline{Pb}$(II) (Pb content of 0.2 meq/g of SA) | 35.6 | 34.9 | 2.5 | 70.5 |
| Run No. 1 of Comparative Example 2 | SA—PbO (PbO content of 0.4 milli-mole/g of SA) | 26.3 | 19.9 | 6.5 | 46.2 |
| Run No. of Comparative Example 2 | SA—PbO (PbO content of 0.2 milli-mole/g of SA) | 29.4 | 25.4 | 9.8 | 54.8 |
| Run No. 3 of Comparative Example 2 | SA | 16.9 | 24.0 | 10.2 | 40.9 |

EXAMPLE 14

Catalysts having a modifying metal ion adsorbed thereon by ion exchange were prepared in substantially the same manner as described in Example 12, and by using the so prepared catalysts, gas phase catalytic reactions were carried out under the same conditions as described in Example 2 to obtain results shown in Table 6. The catalysts used for the reaction are as follows:

Run No. 1:

A catalyst having a manganese content of 0.65 milliequivalent per gram of silica-alumina was prepared in substantially the same manner as described in Example 12 except that 2,000 ml of an aqueous solution containple 12 except that 2,000 ml of an aqueous solution containing 0.2 mole of lead nitrate and 0.1 mole of nickel nitrate was used instead of the aqueous solution of lead nitrate.

Run No. 6:

A catalyst having a silver content of 1.1 milliequivalent per gram of silica-alumina was prepared in substantially the same manner as described in Example 12 except that 2,000 ml of an aqueous solution containing 0.8 mole of silver nitrate was used instead of the aqueous solution of lead nitrate.

Run No. 7:

A catalyst having a copper content of 0.7 milliequivalent per gram of silica-alumina was prepared in substantially the same manner as described in Example 12 except that 2,000 ml of 4 N ammonia solution containing 0.8 mole of cuprous chloride and 1.0 mole ammonium chloride was used instead of the aqueous solution of lead nitrate.

Run No. 8:

A catalyst having a copper content of 0.85 milliequivalent per gram of silica-alumina was prepared in substantially the same manner as described in Example 12 except that 2,000 ml of an aqueous solution containing 0.4 mole of cupric nitrate was used instead of the aqueous solution of lead nitrate.

Run No. 1:

A catalyst containing 0.6 milliequivalent of silver and 0.45 milliequivalent of lead per gram of silica-alumina was prepared in substantially the same manner as described in Example 12 except that 2,000 ml of an aqueous solution containing 0.4 mole of silver nitrate and 0.2 mole of lead nitrate was used instead of the aqueous solution of lead nitrate.

Run No. 2:

A catalyst containing 0.6 milliequivalent of silver and 0.25 milliequivalent of cadmium per gram of silica-

TABLE 6

| | | Yields (%) of Products | | | | |
|---|---|---|---|---|---|---|
| Run No. | Catalyst | Pyridine | 2-methyl-pyridine | 4-methyl-pyridine | high boiling point pyridine bases | pyridine + 2-methyl-pyridine + 4-methyl-pyridine |
| 1 | SA—Mn(II) | 5.0 | 29.5 | 40.1 | 4.6 | 74.6 |
| 2 | SA—Co(II) | 3.0 | 27.8 | 36.2 | 4.3 | 67.0 |
| 3 | SA—Ni(II) | 3.0 | 29.7 | 32.1 | 3.0 | 64.8 |
| 4 | SA—Fe(III) | 3.5 | 28.7 | 32.7 | 2.7 | 64.9 |
| 5 | SA—Pb(II),Ni(II) | 1.2 | 40.8 | 38.6 | 2.8 | 80.6 |
| 6 | SA—Ag(I) | 13.8 | 23.6 | 34.4 | 2.5 | 71.8 |
| 7 | SA—Cu(I) | 10.5 | 21.7 | 30.2 | 2.8 | 62.4 |
| 8 | SA—Cu(II) | 7.4 | 22.8 | 32.4 | 5.6 | 62.6 |

EXAMPLE 15

Catalysts containing tin in an amount of 0.06, 0.25, 0.43 and 0.6 milliequivalent per gram of silica-alumina, respectively, were prepared in substantially the same manner as described in Example 12 except that an aqueous solution of stannous chloride-hydrochloric acid was used instead of the aqueous solution of lead nitrate. Gas phase catalytic reactions were carried out under the same conditions as described in Example 2 by using the so prepared catalysts to obtain results shown in Table 7.

TABLE 7

| | | Yield (%) of Products | | | | |
|---|---|---|---|---|---|---|
| Run No. | Sn Content (meq/g. SA) in SA—Sn(II) Catalyst | 2-methyl-pyridine | 4-methyl-pyridine | total | high boiling point pyridine bases | aceto-nitrile |
| 1 | 0.06 | 31.1 | 32.4 | 63.5 | 3.4 | 1.3 |
| 2 | 0.25 | 42.0 | 38.6 | 80.6 | 2.5 | 4.2 |
| 3 | 0.43 | 34.6 | 29.4 | 64.0 | 2.0 | 12.8 |
| 4 | 0.6 | 25.9 | 20.4 | 46.3 | 1.8 | 23.5 |

EXAMPLE 16

Catalysts having a silver ion and other metal ion indicated in Table 8, which were adsorbed by ion exchange, were prepared in substantially the same manner as described in Example 12, and by using the so prepared catalysts gas phase catalytic reactions were carried out under the same conditions as described in Example 2 to obtain results shown in Table 8. The used catalysts are as follows:

alumina was prepared in substantially the same manner as described in Example 12 except that 2,000 ml of an aqueous solution containing 0.4 mole of silver nitrate and 0.2 mole of cadmium nitrate was used instead of the aqueous solution of lead nitrate.

Run No. 3:

A catalyst containing 0.6 milliequivalent of silver and 0.5 milliequivalent of calcium per gram of silica-alumina was prepared in substantially the same manner as described in Example 12 except that an aqueous solution containing 0.4 mole of silver nitrate and 0.2 mole of calcium nitrate was used instead of the aqueous solution of lead nitrate.

Run No. 4:

A catalyst containing 0.5 milliequivalent of silver and 0.5 milliequivalent of strontium per gram of silica-alumina was prepared in substantially the same manner as described in Example 12 except that 0.4 mole of silver nitrate and 0.2 mole of strontium nitrate were used instead of the aqueous solution of less nitrate.

Run No. 5:

A catalyst containing 0.6 milliequivalent of silver and 0.45 milliequivalent of manganese per gram of silica-alumina was prepared in substantially the same manner as described in Example 12 except that an aqueous solution containing 0.4 mole of silver nitrate and 0.2 mole of manganese nitrate was used instead of the aqueous solution of lead nitrate.

Run No. 6:

A catalyst containing 0.6 milliequivalent of silver and 0.35 milliequivalent of zinc per gram of silica-alumina was prepared in substantially the same manner as described in Example 12 except that an aqueous solution containing 0.4 mole of silver nitrate and 0.2 mole of zinc nitrate was used instead of the aqueous solution of lead nitrate.

TABLE 8

| Run No. | Catalyst | pyridine | 2-methyl-pyridine | 4-methyl-pyridine | high boiling point pyridine bases | pyridine + 2-methylpyridine + 4-methylpyridine |
|---|---|---|---|---|---|---|
| 1 | SA—$\overline{Ag(I),Pb(II)}$ | 12.5 | 38.1 | 37.0 | 2.0 | 87.6 |
| 2 | SA—$\overline{Ag(I),Cd(II)}$ | 11.9 | 35.3 | 36.7 | 2.2 | 83.9 |
| 3 | SA—$\overline{Ag(I),Ca(II)}$ | 12.4 | 34.8 | 40.0 | 3.0 | 87.2 |
| 4 | SA—$\overline{Ag(I),Sr(II)}$ | 12.7 | 26.8 | 37.6 | 2.8 | 77.1 |
| 5 | SA—$\overline{Ag(I),Mn(II)}$ | 13.6 | 26.2 | 35.7 | 2.3 | 75.5 |
| 6 | SA—$\overline{Ag(I),Zn(II)}$ | 10.2 | 27.8 | 35.0 | 2.9 | 73.0 |

EXAMPLE 17

A glass column was packed with 100 ml of ammonium type silica-alumina prepared in substantially the same manner as described in Example 12, and 2,000 ml of an aqueous solution containing 0.4 mole of silver nitrate was developed over a period of 7 days. The so treated silica-alumina was washed with deionized water until the silver ion was not detected in the washing liquid. Then, 2,000 ml of 1 N aqueous hydrochloric acid containing 0.2 mole of stannous chloride was developed over a period of 7 days, and the treated silica-alumina was sufficiently washed with deionized water until no stannous ion was detected in the washing liquid. The so treated silica-alumina was dried and calcined in the same manner as described in Example 12 to obtain a catalyst containing 0.5 milliequivalent of silver and 0.3 milliequivalent of tin per gram of silica-alumina.

By using the so prepared catalyst, a gas phase catalytic reaction was carried out under the same conditions as described in Example 12 to obtain pyridine, 2-methylpyridine and 4-methylpyridine in yields of 10.4%, 33.6% and 34.8%, respectively. The total yield of these products was 78.8% but the yield of high boiling point pyridine bases was only 1.2%.

EXAMPLE 18

Pelletized silica-alumina (having an alumina content of 13%) having a size of 1 mm, which had been calcined at 500° C. for 4 hours in an electric furnace, was dipped in a 1 N aqueous solution of sodium hydroxide for 7 days and then washed with deionized water sufficiently. A glas column having an inner diameter of 30 mm was packed with 100 ml of the so prepared sodium type silica-alumina and 2,000 ml of an aqueous solution containing 0.4 mole of silver nitrate was developed over a period of 7 days. The so treated silica-alumina was washed with deionized water until no silver ion was detected in the washing liquid and it was then dried and calcined in the same manner as described in Example 12 to obtain a catalyst containing 0.6 milliequivalent of silver and 0.4 milliequivalent of Na per gram of silica-alumina.

By using the so prepared catalyst, a gas phase catalytic reaction was carried out under the same conditions as described in Example 2 to obtain pyridine, 2-methylpyridine and 4-methylpyridine in yields of 10.5%, 28.5% and 29.6%, respectively. The total yield of these three products was 68.6% but the yield of high boiling point pyridine bases was only 3.2%.

EXAMPLE 19

By using the same catalyst as prepared in Example 1, the reaction was carried out for 10 hours under the same conditions as described in Example 2 to obtain results shown in Table 9.

TABLE 9

| | ($SiO_2$—$Al_2O_3$—$WO_3$ Catalyst) | | |
|---|---|---|---|
| | Yields (%) of Products | | |
| Time (hours) | 2-methylpyridine | 4-methylpyridine | total |
| 0 | 33.4 | 45.7 | 79.1 |
| 3 | 33.5 | 45.8 | 79.3 |
| 6 | 31.0 | 44.4 | 75.4 |
| 10 | 30.2 | 43.4 | 73.6 |

EXAMPLE 20

By using the same catalyst as prepared in Example 12, the reaction was carried out for 10 hours under the same conditions as described in Example 2 to obtain results shown in Table 10.

TABLE 10

| | (SA—$\overline{Pb}$ Catalyst) | | |
|---|---|---|---|
| | Yields (%) of Products | | |
| Time (hours) | 2-methylpyridine | 4-methylpyridine | total |
| 0 | 43.3 | 39.7 | 83.0 |
| 3 | 43.1 | 39.4 | 82.5 |
| 6 | 42.5 | 38.2 | 80.7 |
| 10 | 41.6 | 38.0 | 79.6 |

COMPARATIVE EXAMPLE 3

By using a silica-alumina catalyst (having an alumina content of 13%), a gas phase catalytic reaction was carried out for 10 hours under the same conditions as described in Example 2 to obtain results shown in Table 11.

TABLE 11

| | (SA Catalyst) | | |
|---|---|---|---|
| | Yields (%) of Products | | |
| Time (hours) | 2-methylpyridine | 4-methylpyridine | total |
| 0 | 16.9 | 24.0 | 40.9 |
| 3 | 16.5 | 23.3 | 39.8 |
| 6 | 14.9 | 21.5 | 36.4 |
| 10 | 12.6 | 17.5 | 30.1 |

What is claimed is:

1. A process for preparing pyridine bases from acetaldehyde and ammonia by gas phase catalytic reaction, wherein the gas phase catalytic reaction is carried out at a temperature of 300° to 550° C. and at a space velocity of 200 to 10,000 $hr^{-1}$ in the presence of a catalyst prepared by subjecting silica-alumina to ion exchange with ions of a member selected from the group consisting of manganese, nickel, iron, cobalt, silver, copper and silver plus sodium to adsorb the ions on said silica-alumina wherein the silica/alumina weight ratio is in the range of from 98/2 to 50/50 and wherein the catalyst contains the ions in an amount of 0.01 to 1.2 milliequivalents per gram of silica-alumina.

2. A process for preparing pyridine bases according to claim 1 wherein said ions are nickel or iron ions and are present in an amount of 0.1 to 0.5 milliequivalent per gram of the silica-alumina.

3. A process for preparing pyridine bases according to claim 1 wherein said ions are manganese, cobalt, silver or copper ions and are present in an amount of 0.1 to 1.2 milliequivalents per gram of the silica-alumina.

4. A process for preparing pyridine bases according to claim 1 wherein said ions are monovalent silver or copper ions.

5. A process for preparing pyridine bases according to claim 1 wherein the catalyst is one prepared by dipping silica-alumina in aqueous ammonia to convert acid sites of the silica-alumina to the ammonium type and adsorbing said ions on the silica-alumina by cation exchange.

6. A process for preparing pyridine bases according to claim 5 wherein the catalyst is one prepared by adsorbing said ions on the ammonium type silica-alumina by cation exchange according to the column method.

7. A process for preparing pyridine bases according to claim 1 wherein acetaldehyde and ammonia are separately preheated to a temperature of at least 200° C. and then, they are mixed together and contacted with the catalyst.

8. A process for preparing pyridine bases according to claim 1 wherein a gas mixture of the acetaldehyde and ammonia is preheated to 300° to 550° C. before the mixture is contacted with the catalyst.

9. A process for preparing pyridine bases according to claim 1 wherein the molar ratio of the ammonia to the acetaldehyde is 0.5 to 3.0.

10. A process for preparing pyridine bases according to claim 1 wherein the gas phase catalytic reaction is carried out in the presence of at least one diluent selected from the group consisting of steam, helium, argon and nitrogen.

11. A process for preparing pyridine bases according to claim 1 wherein the reaction temperature is in the range of from 350° to 500° C.

12. A process for preparing pyridine bases according to claim 1 wherein the space velocity is in the range of from 400 to 2,000 $hr^{-1}$.

* * * * *